United States Patent
Wells et al.

[11] Patent Number: 5,835,211
[45] Date of Patent: Nov. 10, 1998

[54] SINGLE-PARTICLE OPTICAL SENSOR WITH IMPROVED SENSITIVITY AND DYNAMIC SIZE RANGE

[75] Inventors: David Wells, Silver Spring, Md.; David F. Nicoli, Goleta, Calif.

[73] Assignee: Particle Sizing Systems, Inc., Santa Barbara, Calif.

[21] Appl. No.: 625,540

[22] Filed: Mar. 28, 1996

[51] Int. Cl.$^6$ .......................... G01N 15/02; G01N 21/00
[52] U.S. Cl. .................. 356/336; 356/335; 356/337; 356/338; 356/343
[58] Field of Search ........................... 356/336–343; 250/574, 576, 564, 565; 377/11, 10

[56] References Cited

U.S. PATENT DOCUMENTS

| | | | |
|---|---|---|---|
| 3,960,449 | 6/1976 | Carleton et al. | 356/103 |
| 4,735,504 | 4/1988 | Tycko | 356/336 |
| 4,794,806 | 1/1989 | Nicoli et al. | 73/863 |
| 4,842,406 | 6/1989 | VonBargen | 356/336 |
| 4,953,978 | 9/1990 | Bott et al. | 356/336 |
| 4,986,659 | 1/1991 | Bachalo | 356/336 |
| 5,056,918 | 10/1991 | Bott et al. | 356/336 |
| 5,090,808 | 2/1992 | Ishikawa et al. | 356/336 |
| 5,416,580 | 5/1995 | Trainer | 356/336 |
| 5,561,515 | 10/1996 | Hariston et al. | 356/28 |

*Primary Examiner*—Frank G. Font
*Assistant Examiner*—Michael P. Strafira
*Attorney, Agent, or Firm*—Milton M. Field; Charles H. Schwartz

[57] ABSTRACT

An optical sensor for counting and sizing particles, including a light extinction (LE) signal representative of the particles, and a light scattering (LS) signal representative of the particles. The light scattering signal and the light extinction signal are combined to form a single composite signal. The single composite signal has a substantially similar output to the light extinction (LE) signal for particle sizes in an upper range of particle sizes typically measured by the light extinction sensor. The single composite signal has a substantially similar output to the light scattering (LS) signal for particle sizes in a lower range of particle sizes typically measured by the light scattering sensor. The single composite signal has an output representing the combined light extinction (LE) signal and light scattering (LS) signal for particle sizes in a middle range of particle sizes.

16 Claims, 5 Drawing Sheets

FIG. 7

SINGLE-PARTICLE OPTICAL SENSOR WITH IMPROVED SENSITIVITY AND DYNAMIC SIZE RANGE

FIELD OF THE INVENTION

The present invention relates to a single-particle optical sensor for measuring the size of particles suspended in either liquid or gas.

INTRODUCTION

The technique of single-particle optical sensing (SPOS) is an effective, well-established method for counting and sizing particles suspended in either liquid or gas. This technique has been used successfully in two major areas of applications. In the first area, the SPOS method has been used extensively to detect and quantify contaminant particles in gases and liquids. Popular examples include cleanroom air, injectable pharmaceutical parenterals, hydraulic oils, semiconductor process fluids and potable water.

In the second area, the SPOS technique has also been used successfully to determine the particle size distribution (PSD) of a wide variety of particulate-based compounds and final products. Here, by contrast, the focus of interest is the size distribution of specialized particles which have been explicitly manufactured, rather than contaminant particles which coincidentally exist and which one wishes to exclude. Applications for "particle size analysis", in this most general sense, are varied and numerous, including virtually all dry powders, particles suspended and/or dispersed in water or organic solvents, and oil-in-water or water-in-oil emulsions. For these applications of the SPOS technique, the starting particle concentration is, by definition, very high, requiring that the starting material be diluted—either in liquid or gas, whichever is appropriate—to a concentration sufficiently low to permit reproducible and accurate measurement.

BACKGROUND OF THE INVENTION

For most applications involving the SPOS technique, one wishes in general to obtain the widest possible size range— i.e. the lowest possible minimum diameter and highest possible maximum diameter—through the use of a single sensor. However, the two traditional approaches to particle size analysis using SPOS have conflicting characteristics and requirements. On the one hand, a light scattering (LS) approach is needed in order to extend the sensitivity of the method to the smallest possible particle diameters, using more powerful light sources and/or more efficient optical systems for collecting a larger fraction of the total scattered light intensity. However, there are two drawbacks inherent in an LS sensor design; the first represents a practical inconvenience, while the second is a fundamental limitation.

The first limitation is that the sensor response, dV, is highly dependent on the index of refraction and absorbance of the particle. The larger the difference in the indices of refraction of the particle and surrounding solvent (liquid or gas), the larger the scattered light intensity signal, dV. The larger the absorbance of the particle, the smaller the scattered intensity signal.

The second, more fundamental, limitation is that the dynamic range of an LS sensor is inherently quite limited. The sensor response, dV, quickly "saturates" with respect to increasing particle diameter, meaning that the resolution becomes relatively poor at the highest diameters. That is, relatively large increases in particle diameter result in relatively small changes in sensor detector response, dV. The underlying reason for this behavior is the strong dependence of the scattered light intensity response, dV, on the particle diameter, d, as discussed further below.

In the Rayleigh region, defined by $d<<\lambda$ (i.e. $d \leq 0.1$ um), the scattering response, dV, increases with the 6th power of d. A numerical example would be useful. Let us suppose that the pulse height, dV, corresponding to the minimum detectable particle diameter, $d_{min}$, is 1 mV. (This is overly optimistic, given typical noise levels for SPOS sensors of approx. 5 mV.). The maximum particle diameter which can be sized is defined by the signal level at which the signal-conditioning amplifier is "saturated", reaching $V_o$, typically 10 Volts. This represents a factor of 10,000 increase over the signal produced by the smallest detectable particle. Given the 6th power dependence of signal dV on diameter d, this implies a maximum measurable diameter which is only about 5 times larger than $d_{min}$.

However, with increasing particle diameter, larger than 0.15–0.2 um, one enters the region of Mie scattering, where intraparticle interference can significantly reduce the magnitude of the net scattered intensity signal, dV, produced by a particle in an LS sensor. As d increases, mutual interference of the scattering "wavelets" within the particle causes the effective scattering volume to decrease, resembling an outer "shell", with signal dV increasing only like the 4th power of d. For these larger particles a 10-fold increase in d is required in order to obtain the same 10,000-fold increase in the signal, dV, which presumably results in saturations.

The conclusion is clear: an LS sensor necessarily possesses a very "steep" response characteristic of log dV vs log d, which severely limits the maximum particle diameter which can be measured in practice before saturation is reached. To compensate for this problem, it is well known that one can use electronic "compression" circuitry (typically through the use of one or more nonlinear circuit elements, together with other passive and/or active electronic elements) to "roll off" the slope of the response curve, log dV vs log d, so that considerably larger diameters can be measured before the scattering signal, dV, reaches saturation, $V_o$.

Hence, there is a price to pay for extending the effective range, or maximum diameter limit, of an LS sensor using such compression techniques: reduced resolution. The resolution of the sensor, defined by the change in particle diameter needed to produce a given magnitude change in the response, dV, is significantly and necessarily compromised through the use of compression techniques, whether they employ analog or digital schemes. Relatively large changes in particle diameter will therefore produce correspondingly smaller changes in sensor response signal, dV, resulting in reduced sensor performance.

Hence, in practice, an LS sensor which has a lower effective detection limit of, say, 0.5 um (referenced to "standard" polystyrene latex particles) generally can be expected to have a practical upper diameter limit of only 10–20 um, depending on the optical design and electronic compression scheme employed. For sensor designs which push down the lower detection limit to a smaller size, e.g. 0.2 um, there is a corresponding decrease in the maximum, practical upper limit in size, typically to 5–10 um, or lower. Hence, for LS sensor designs, improved sensor sensitivity, or lower size limit, is necessarily obtained at the expense of a significant decrease in the upper size limit.

In fairness to the capability of LS sensor designs, it must be acknowledged that for the most demanding applications in contamination monitoring, requiring extreme sensitivity limits of 0.1–0.2 um, or even lower, there may be no practical need for a high maximum diameter limit (i.e. above a couple of microns). This is, presumably the solutions to be analyzed are already so "clean" that they no longer possess measurable concentrations of the larger particles. However, for many applications in particle size analysis involving specialty materials, especially those which require the measurement of a highly "polydisperse" particle size distribution (PSD), containing a wide range of sizes, it is feasible, but not acceptable, to sacrifice the upper diameter limit of the sensor in favor of a lower minimum diameter limit.

Therefore, a light extinction (LE) sensor is generally preferred over one based on light scattering (LS) in order to permit effective particle size analysis over the large size range which would be required for an analytical instrument of general applicability. There are two fundamental reasons for the attractiveness of an LE sensor for general particle size analysis. First, compared to an LS sensor design, it is more suitable for sizing particles over a large size range, notwithstanding one's ability to extend the maximum size limit of an LS sensor through the judicious use of electronic compression circuitry. The maximum particle diameter which can be accurately and effectively sized using an LE sensor design is arbitrarily large, limited only by the lateral dimensions of the flow channel and the rolloff characteristics of the calibration curve. The minimum diameter is typically smaller than 1% of the maximum, with the actual lower limit dependent on the signal/noise performance of the system.

The second reason why an LE sensor is so attractive for general particle size analysis is that its response, for all but the smallest particle diameters in its range of effectiveness, is relatively insensitive to the composition of the particles being measured, as discussed in the Introduction above. While not providing a completely "absolute" measurement of particle size, independent of particle composition, the LE method nevertheless represents a simple, highly attractive technique for analyzing the PSDs of a wide variety of particulate systems, covering a wide range of particle diameters, starting at approx. 1.5 um.

The difficulty, of course, is that there are many particle sizing applications of great interest for which the PSD covers an "inconvenient" range of particle diameters—e.g. from below one micron to larger than 25 um—which is not completely accessible by the SPOS technique using either an LS or LE sensor alone. The challenge, is to combine the best, defining characteristics which are provided by each type of sensor. On the one hand, one needs the high sensitivity which is offered by an LS sensor, in order to achieve the lowest practical minimum diameter, below one micron. On the other hand, one needs the arbitrarily high maximum size and relative insensitivity to particle composition which is offered by an LE sensor.

In the past there have been two approaches to resolving this need for both LS and LE sensor responses in the design of practical SPOS instrumentation for particle size analysis over the broadest possible size range. First, there has been a "brute-force" approach, consisting simply of using both LS and LE sensors to analyze the same sample, or representative portions (replicates) of the same sample, in a sequential fashion. The resulting "pieces" of the PSD obtained using each sensor must then be suitably "joined", or added together, so that a convincing overall distribution is thereby produced. In practice, this process entails modifying the portion of the PSD obtained from the LS sensor in order to take into account as best as possible the effects on the log dV vs log d response curve due to differing index of refraction and/or absorbance of the actual samples particles compared to the "standard" particles (typically polystyrene latex) used to make the calibration curve.

Obviously, this "brute force" approach is unattractive for several reasons. First, two completely different sensors are required, adding significantly to the cost and complexity of the resulting instrument system. Second, the overall time required for the sample analysis in practice is increased by more than a factor of two. The measurement, in effect, must be made twice, once with each sensor, followed by manipulation, or "massaging" of the PSD data, using an appropriate mathematical algorithm, in order to "connect" correctly and optimally the two sets of data, thereby producing the best overall PSD result.

A second approach to the problem of having to choose between an LS and LE sensor response has been outlined in U.S. Pat. No. 4,842,406 of VonBargen. The invention of VonBargen consists of a sensor design which, in effect, consists of two separate sensors which are contained within a single physical housing. When a particle passes through an active sensing zone, or view volume, three separate "signals" are produced by the two different sensing systems embedded in the sensor.

The first signal is the same as that normally produced in a typical generic LS sensor design. The second signal described by VonBargen is the same as that normally produced in a typical LE sensor design. In addition, the sensor design described by VanBargen includes a third signal, consisting of the width, in time, of the pulse produced by the LE portion of the system. This yields the transit time of the particle as it passes through the active view volume.

The essential innovation in the VonBargen invention is an electronic means for performing an automatic, real-time decision-making process for each particle which passes through the active sensing view volume of the sensor. The system automatically chooses which of the three sensor detector responses, or signals, to use for the analysis, depending on the size of the response. The latter, in turn, depends on the size range where the particle is determined to be. For a particle in the size range of 0.5 to 10 microns, the system electronically compares the three different signal responses produced by the particle and concludes that the signal output from the LS sensor is appropriate. For a particle in the size range of 10–50 um, the electronic system makes the determination that the most appropriate signal of the three which are available is the one produced by the LE sensor. Finally, as mentioned above, VonBargen adds a variation on the standard LE approach for sizing relatively large particles. This involves accessing a third piece of information contained in the LE signal response: the width, in time, of the pulse produced by passage of the particle across the active view volume—i.e. the transit time of the particle. This third "signal", or piece of information, is automatically selected in the VonBargen invention whenever the particle diameter exceeds 50 um, determined when the pulse height obtained from the LE sensor exceeds a certain value.

In summary, the VonBargen invention achieves a lower size limit and wider dynamic size range by improving upon the "brute force" approach outlined above. The two separate sensors—one of LS design and the other of LE design—are combined into the same package, utilizing the same active view volume. However, owing to the use of an electronic system which can simultaneously compare the three relevant signals produced by the VonBargen design, the measurement by each sensor does not have to be repeated. Real-time comparison of the three pulse signals created by the passage of a particle through the active view volume allows the system to decide which of the three signals to use when producing the final PSD result.

Unfortunately, the VonBargen invention possesses at least one significant, inherent disadvantage. The "pasting together" of two separate portions of particle size distributions very likely will result in a significant discontinuity in the resulting number distribution, whether cumulative or differential. The effects on the corresponding area-weighted or volume-weighted PSDs will be even greater and more disturbing. The extent of the shifts and discontinuities will depend greatly on changes in the optical properties of the sample particles relative to the standard calibration particles. The very nature of the VonBargen invention results in an abrupt discontinuity, or "mismatch", between the portions of the PSD—a juxtaposition of two disparate results.

What is needed, instead, is to apply a more gradual transition between the response, log dV vs log d, produced by an LS sensor and that produced by an LE sensor. The hard transition which is an unavoidable consequence of the VonBargen design must be avoided, if possible. In addition, in general it is always preferable to favor the LE response over the LS response, owing to the greater insensitivity of the former to changes in the optical properties of the sample particles under investigation. As was already discussed in the Introduction, LE sensors are well known to be effective down to diameter of approximately 1.5 um (referenced to polystyrene latex). Therefore, the VonBargen design suffers in at least two respects. First, it necessarily yields a "hard" crossover, resulting in a sharp discontinuity between the portions of the PSD obtained from the individual LS and LE responses for all particle systems which differ in optical properties from those of the calibrating standards. Second, the crossover diameter, $d_{cross}$, for switching between the two responses which is suggested by VonBargen is too high, by a considerable amount, relative to the effective lower diameter limit which is easily achievable using an LE design.

In the invention described below, we obtain considerably superior results for "real" distributions of particles, effectively eliminating the sharp discontinuities present in the VonBargen design. Also, as a consequence of the novel design which we propose, we require an electronic circuit design which is significantly simplified, relative to that which is required in the scheme proposed by VonBargen.

SUMMARY OF THE INVENTION

In the invention herein described, the desirable, mutually exclusive characteristics of the LS and LE sensor responses are combined, so as to yield a final sensor response which, by definition, offers the best features of these two SPOS methods of particle detection and size analysis.

The new and novel approach which is made in the present invention consists of simultaneously combining both the LE and LS response signals by simple electronic means, in a particular way. The resulting composite signal can then be easily and efficiently analyzed, thereby yielding a good approximation of the size of each detected particle over the entire size range covered by either the LS or LE methods.

DETAILED DESCRIPTION OF THE DRAWINGS

Figure 1:
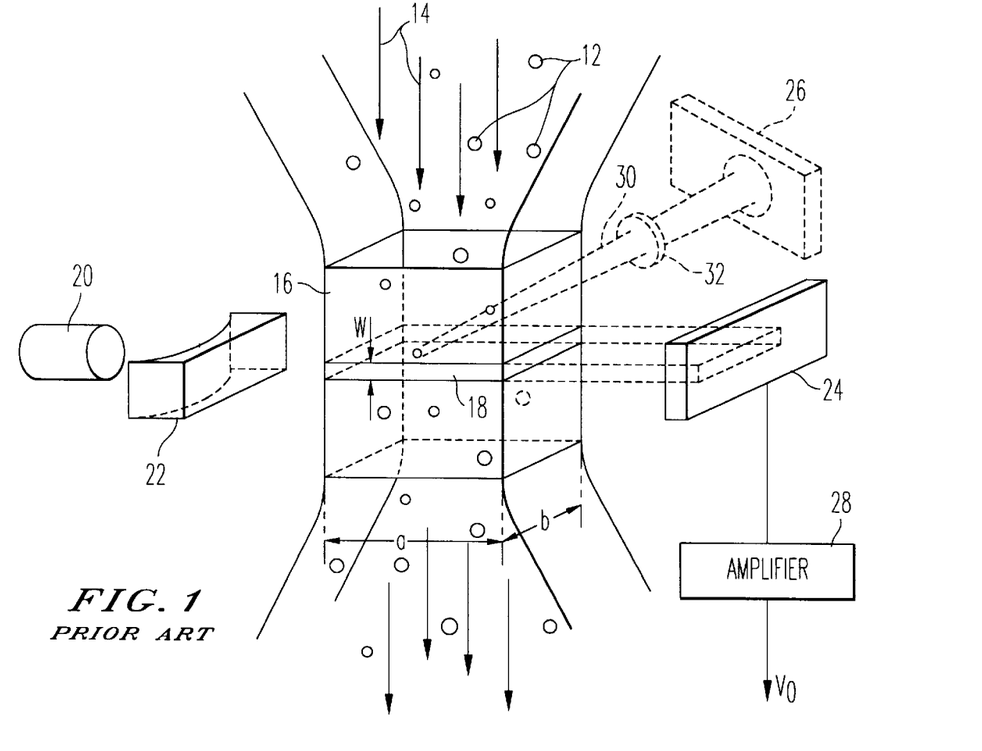
FIG. 1 illustrates a typical prior art system for detecting particles using either light extinction (LE) or light scattering (LS)

The principles of operation which underlie the conventional (existing) SPOS technique are conceptually simple and, for the most part, well understood. However, a brief review of underlying principles is useful. As shown in FIG. 1, fluid 10, either gas or liquid, in which particles 12 to be detected and measured are suspended, is caused to flow at a predetermined rate of flow, F. This is shown by arrows 14 through a physical "flow channel" 16, defined by lateral dimensions a and b. A thin, sheet-like beam of light 18 of approximately uniform intensity with respect to the lateral dimension (b), and having a thickness w, is established across the flow channel, normal to its axis, through the use of a suitable light source 20 (e.g. laser diode) and optical elements 22 (e.g. cylindrical lens). Typically, the intensity variation across the thickness, w, of the sheet-like beam of light 18 follows an approximately gaussian profile.

This thin "sheet", or "slab", of illumination 18, together with the walls of the flow channel, defines the "view volume" of the sensor. A light-sensitive detector 24 or 26, typically of miniature, solid-state design, is suitably located with respect to the source of illumination and the view volume so as to be able to detect any particle which arrives within the view volume, as a consequence of the fluid flow, as will be described shortly. The positioning of the detector, as well as associated optical elements, if required, is designed to optimize the correlation between the detector output signal and the mean diameter of the particle which has been detected, thereby maximizing the accuracy and resolution of the sensor for determination of particle size.

There are two methods which have been used extensively to detect and size particles which pass through the view volume of an SPOS-type sensor. Implementation of these two methods has resulted in two very different sensor designs, as is well known in the SPOS field. Choice of one or the other of these sensing methods has been dictated by the desired range of particle size.

The first, and most straightforward, method of single-particle sensing is generally referred to as the method of light blockage ("LB"), or light obscuration ("LO"), but is more correctly called light extinction ("LE"). This method is commonly used to detect and size particles over the size range which extends from arbitrarily large diameters (i.e. limited only by the lateral dimensions of the flow channel of the LE sensor) down to approximately 1.5 microns (um). The second method, which is that of light scattering ("LS"), has been used to detect and size particles over a size range extending from a few microns (i.e. as high as 20–25 um)

down to as small as 0.1 um, or even smaller. We shall briefly review these two methods, which form the essential ingredients of the present invention.

In the light-extinction (LE) method, the detector 24 ($D_{LE}$) is placed opposite the light source 20, on the other side of the flow channel 16, so that the fluid 16 containing the suspended particles 12 flows between the light source and the detector 24, ($D_{LE}$). The sheet-like beam of light 18 incident on the detector 24 ($D_{Le}$) produces an output signal, after suitable amplification by amplifier 28, of strength $V_o$. The strength of the signal produced by the detector 24 depends on the intensity of the light source 20 (typically a laser diode or incandescent lamp), the sensitivity of the detector 24, the gain of the amplifier 28 and the cross-sectional area of the illuminated view volume, equal to the product w×b (FIG. 1). Typically, the amplifier gain is adjusted to yield a final output level $V_o$ of 10 volts, consistent with the useable maximum signal level of most commercially available operational amplifiers.

When a suspended particle 12 enters the thin view volume 18, it effectively "blocks" a small fraction of the incident light beam, preventing that fraction of incident illumination from reaching the detector 24 ($D_{Le}$). This action causes the amplified detector output signal to decrease by a small amount, dV. The extent of this decrease in detector signal, dV, is strongly correlated with the mean diameter of the particle for an LE-type sensor. Provided the latter has been properly designed, the extent of the decrease in detector signal output, dV, caused by the passage of a particle into the view volume will increase smoothly and monotonically with the mean diameter of the particle over a large dynamic size range—e.g. 1.5 to 400 um, a convenient range for contamination analysis.

By contrast, for the light scattering (LS) method, the detector 26 is located away from the path of the thin light beam 18 which traverses the flow channel 16 of the sensor. This detector 26, which we refer to as $D_{LS}$, is ideally able to receive only the amount of light 30 which has been scattered from a particular region within the small illuminated view volume of the sensor. The size, shape and orientation/location of the detector 26 ($D_{LS}$) and associated collection optics 32 will determine the range of scattering solid angles that contribute to the resulting scattered light signal.

Unlike the case of an LE-type sensor, the LS signal produced by detector 26 ($D_{LS}$) is ideally zero in the absence of a particle in the illuminated view volume. Passage of a particle 12 through the latter causes the incident light beam to be scattered momentarily over all angles, resulting in a signal pulse, dV, at the output of detector 26 ($D_{LS}$). The magnitude, or height, of pulse dV depends on the size and optical properties (i.e. index of refraction and absorbance) of the particle in question, as well as the range of scattering angles defined by the scattering collection optics and detector. Again, as in the case of an LE-type sensor, the height of dV is strongly correlated with the mean diameter of the particle. However, unlike the case of light extinction, it is also highly dependent on the optical properties of the particle. Provided the sensor 26 ($D_{LS}$) has been properly designed, the magnitude of dV is expected to increase smoothly and monotonically with the mean diameter of the particle. Unfortunately, in an LS-type sensor this required behavior will generally be achieved over a substantially smaller dynamic size range than can be expected for an LE-type sensor—from 0.1 or 0.2 um to only 20–30 um.

First, we focus on the properties of an LE-type sensor. There are three predominant physical mechanisms by which a particle located within the view volume causes a fraction of the incident light to be prevented from reaching the detector in an LE sensor. These include refraction (i.e. deflection), absorption and scattering. The first mechanism is usually the most important for particles which are substantially larger than the wavelength, $\lambda$, of the illuminating light source—i.e. diameters larger than a few microns. Incident light is refracted, or deflected, away from the forward direction of the detector $D_{LE}$ because the particle acts like a short-focal-length lens, owing to the (presumed) difference in its index of refraction from that of the surrounding fluid, liquid or gas. The great advantage of this mechanism is that particles of a given size usually produce quite similar decreases in detector signal, dV, despite having significantly different compositions or indices of refraction. The incident light which impinges on a particle is generally deflected enough so that it fails to reach the detector $D_{LE}$, regardless of the precise angle or extent of deflection (both of which depend on the index of refraction of the particle).

The second physical mechanism which occurs in an LE sensor is that of light absorbance, caused by pigmenting or some other specific absorption mechanism. This phenomenon, which is independent of the index of refraction of the particle, causes partial attenuation of the light incident on the particle, which would otherwise pass through the particle, thereby causing a decrease in the overall amount of light reaching the detector $D_{LE}$.

Finally, there is the physical mechanism of light scattering, alluded to above, which occurs universally for particles of all sizes, provided there is a difference in the indices of refraction of the particle and the surrounding fluid. A small fraction of the light which is incident on the particle is reradiated by the polarizable electrons in the particle, giving rise to a spatial pattern of scattered light. The portion of the scattered light which is not propagated in the forward direction will fail to reach the detector $D_{LE}$, thereby contributing to the overall decrease in detector signal, dV. The effect of the scattering mechanism in reducing the amount of incident light which reaches the detector is typically much smaller than that produced by the mechanisms of refraction and absorbance, except for the smallest particles—i.e. those smaller than a few microns.

The net "extinction" signal, dV, is the result of the combination of all three physical mechanisms. In general, the magnitude of this signal is a function of the size, shape and orientation of the particle in question and also, to a lesser extent, of its specific composition.

The principle which underlies particle detection and sizing using the SPOS technique is very simple. A liquid or gas containing the suspended particles of interest is directed through the SPOS sensor at a substantially constant flow rate—typically between 25 and 250 cc/min for liquids containing particles smaller than 500–1000 um. The concentration of particles is adjusted to be sufficiently low that there is a negligible probability of having more than one particle located within the view volume at any given time. That is, the particle concentration is assumed to be well below the "coincidence limit" of the sensor. The latter is defined by the size of the view volume—i.e. its thickness, w, multiplied by the cross sectional area of the flow channel, a×b (FIG. 1).

For applications involving "contaminant" particles, the concentration of detectable particles is generally well below the coincidence limit of the sensor. However, for particle-sizing applications involving manufactured particles, the starting concentration of the sample is almost always too high, requiring significant dilution of the sample, either in the dry or liquid-suspended state. A simple, effective and automatic method for diluting particles in either liquid or gaseous suspension has been described previously, in U.S. Pat. No. 4,794,806 and related foreign patents of Nicoli et al.

When a particle traverses the sheet-like view volume 18 of the sensor, a negative-going pulse of height dV is created, superimposed on the "background" level $V_o$, which corresponds to the absence of any particles and resulting extinction of signal. The larger the particle, the more extensive the extinction effect (as a result of the three mechanisms described above), and therefore the larger the decrease in detector signal from its quiescent, original value, $V_o$, and the larger the pulse height, dV. The width in time of the resulting pulse is essentially given by the transit time of the particle across the thin dimension of the view volume. For typical LE sensor designs, with dimension w in the range of 25–50 um, the typical pulse width, assuming a fluid flow rate of 60 ml/min, is 10 to 20 microseconds.

For particle diameters substantially larger than the illuminating wavelength, λ, but smaller than the width, w, of the view volume, the pulse height, dV, is approximately proportional to the projected cross-sectional area of the particle. While this quantity in general depends on the shape and orientation of the particle in question, it is simple in the case of a spherical particle: dV is proportional to the square of the particle diameter. For particles substantially larger than the width, w, of the view volume, the dependence of the pulse height on the particle diameter is closer to linear than quadratic.

Figure 2:
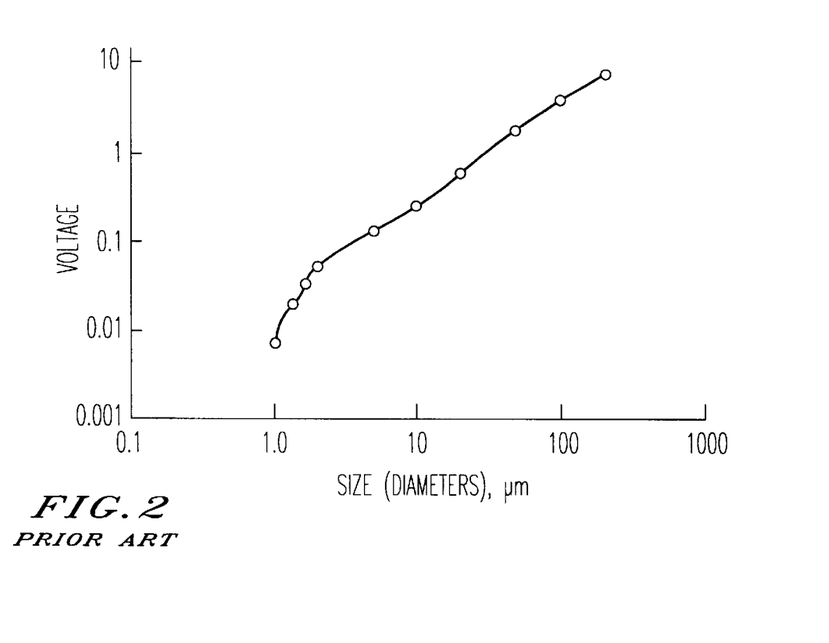
FIG. 2 shows a typical calibration curve for an LE sensor.

Therefore the "calibration curve" for an LE sensor, which describes the pulse height, dV, as a function of particle diameter, d, ideally resembles a smooth, somewhat curved (concave down) plot on a graph of log dV vs log d. In actuality, the extent of the curvature is often substantially modified through the use of nonlinear elements (e.g. diodes) with signal-conditioning amplifiers. These circuits change the amplifier gain, or sensitivity, as a function of the original pulse height, resulting in a modified response, or calibration curve, of log dV vs log d. For example, the intentional "rolloff", or reduction in the slope of, the calibration curve log dV vs log d has the effect of extending the maximum useful diameter range of the sensor—the diameter at which the magnitude of dV reaches $V_o$ (or the diameter which equals the minimum cross-sectional dimension of the flow channel (a or b in FIG. 1), whichever is reached first). FIG. 2 shows a typical calibration curve for an LE sensor which covers the size range of 1.5 to 400 um, obtained using uniform polystyrene latex particles of various sizes.

Notwithstanding the advantages conferred on the SPOS technique by the VonBargen invention, outlined above, there remain some significant disadvantages inherent in that proposed design. First, there is the complexity of electronic circuitry implicit in the VonBargen design. There are three separate signals, requiring a fairly sophisticated signal processing system and associated decision-making logic, to automatically choose the appropriate signal for final processing, each time a particle passes through the active view volume of the sensor In short, the schematic diagram of the resulting electronic system required to implement this approach, summarized in FIG. 2 of VonBargen's U.S. Pat. No. 4,842,406, is not particularly simple.

Figures 3A, 3C:
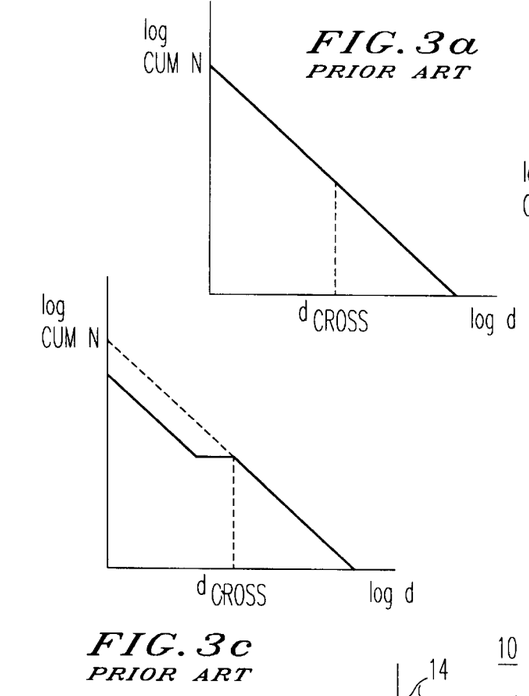
FIG. 3a shows a simplified idealized population distribution for a very broad size distribution of particles.
FIG. 3c shows a second type of discontinuity which can occur in prior art sensors.

More important, the signal processing system required by VonBargen does not possess the flexibility required in order to produce acceptable PSD results for the wide variety of sample types which are encountered for typical particle sizing applications. Two examples illustrate this point. FIG. 3a shows a simplified, idealized cumulative population distribution which resembles the result often obtained for a very broad size distribution of particles, ranging from many microns down to submicron sizes. One example: "AC Fine Test Dust" (Arizona desert road dust). This result, representing the cumulative number of particles, N, which are smaller than a given diameter, d, is plotted in FIG. 3a as log cum N vs log d. For "ideal" broad distributions of particle sizes, this logarithmic plot is frequently observed to be approximately linear, as shown ideally in FIG. 3a. This plot serves as a convenient reference for understanding the adverse influence which variability in sample composition, or optical properties, has on the performance of the sensor design proposed by VonBargen.

Provided the sample under investigation has the same index of refraction and absorbance as the particles which are used to calibrate the individual light scattering (LS) and light extinction (LE) responses of the VonBargen sensor system, there will be a smooth transition at the "crossover" diameter, $d_{cross}$, which connects the two portions of the particle size distribution produced by the individual LS and LE portions of the system. For particle diameters, d, larger than $d_{cross}$, the signal produced by the LE subsystem (i.e. pulse height for diameters larger than 10 um but smaller than 50 um, but pulse widths for diameters larger than 50 um and smaller than 300 um) is utilized to count and size the particles, using the appropriate calibration curve.

For particles smaller than $d_{cross}$, the signal produced by the LS subsystem (i.e. pulse height) is used to count and size the particles, using the appropriate calibration curve. Because the particles of the sample are presumed to produce the same signal response, LS or LE, as the particles used to produce the respective calibration curves, there should necessarily be no discontinuity between the two portions of the resulting PSD, for d<$d_{cross}$ and d>$d_{cross}$, as illustrated in FIG. 3a. However, for sample particles with optical properties substantially different from those of the "standard" particles used to calibrate the LS and LE responses of the VonBargen sensor, the resulting PSD is not as well behaved as the ideal situation depicted in FIG. 3a.

For the first example, we take the case of particles which have the same absorbance as the standard particles used to calibrate the system (e.g. very low absorbance, in the case of polystyrene latex beads), but a significantly higher index of refraction, compared to the standard particles. (For the sake of simplicity, the refractive index of the latter is presumed to be higher than that of the suspending solvent.) In this case, one would expect to obtain a cumulative PSD which resembles that shown in FIG. 3b. Here, the fact that the sample particles provide a higher "contrast" to the solvent than that of the standard particles, by virtue of their higher refractive index, means that they scatter light more strongly than the latter, for a given diameter. Hence, these "brighter" particles will be over-sized by the LS portion of the VonBargen sensor.

Figure 3B:
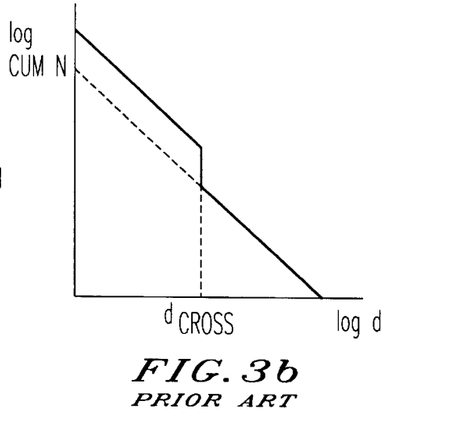
FIG. 3b shows a first type of discontinuity which can occur in prior art sensors.

However, as has already been discussed, the LE portion of the VonBargen sensor produces a signal which is relatively insensitive to the increase in refractive index of the sample particles. Therefore, the size distribution produced by the LE signal for diameters larger than the crossover diameter, $d_{cross}$, (e.g. 10 um, as specified in the VonBargen Patent) should be approximately "correct". The result: a significant discontinuity in the cumulative population, or number, distribution for the sample particles. This is shown in FIG. 3b by the shift in the LS-generated portion of the PSD, with a vertical "jump" occurring at the crossover diameter, $d_{cross}$, of course, the differential PSD will exhibit a corresponding discontinuity. The larger the difference in the index of refraction of the sample particles relative to that of the calibration particles, the more extensive will be the extent of the discontinuity in the overall PSD, and systematic oversizing of particles smaller than $d_{cross}$.

For the second example, we consider sample particles which are more closely matched to the solvent, in index of refraction, than those of the standard, calibrating particles. Here, there is a corresponding, but opposite, shift in the computed PSD. In this case, the smaller particles in the distribution, $d<d_{cross}$, will be under-sized. The same kind of undesirable shift and discontinuity in the computed, composite PSD will occur in the case of particles which absorb light more strongly than those used to calibrate the LS and LE portions of the VonBargen sensor. The consequences of this second example are shown schematically in FIG. 3c. Here, a distinct "flat" region occurs in the cumulative distribution. This corresponds to a "hole" in the corresponding differential distribution—i.e. essentially no particles are detected over the range of diameters encompassed by the flat region in FIG. 3c.

Figure 4:
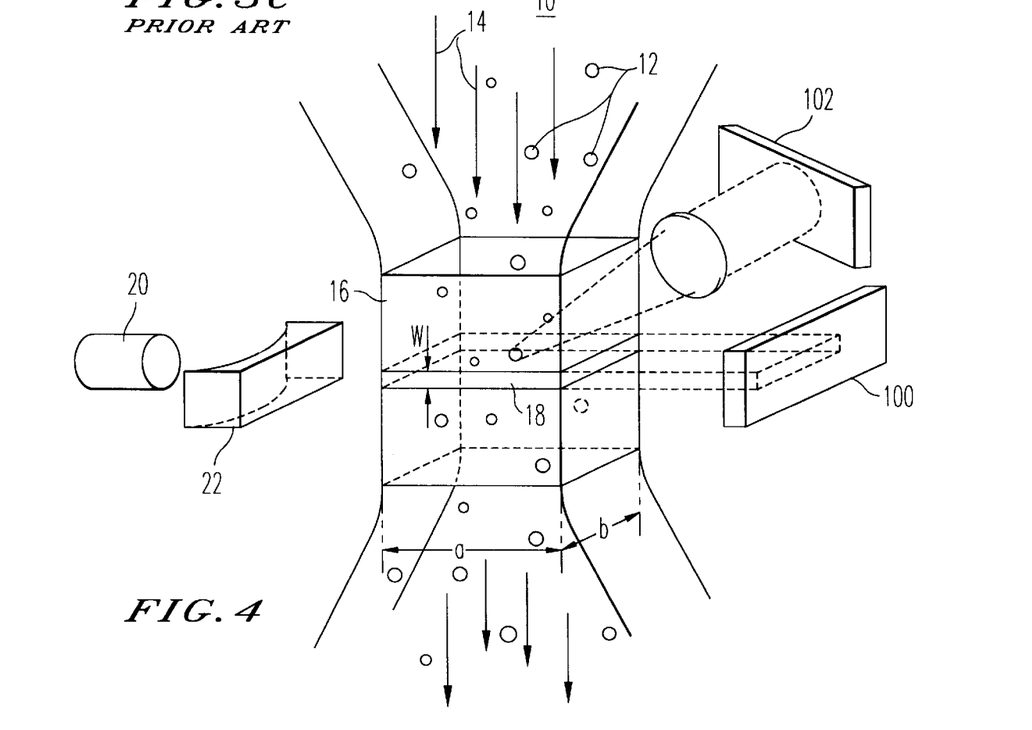
FIG. 4 illustrates a preferred embodiment of the present invention.

The design of the sensor which represents a preferred embodiment of the present invention is shown schematically in FIG. 4. It contains the usual light source 20 (typically a laser diode) and the simple optical system 22 (e.g. collimating optics plus cylindrical lens), which can generate the thin, sheet-like beam of light 18 of approximately uniform intensity with respect to the lateral dimension, b, across the flow channel 16, as described above. Our new sensor design then uses two or more detectors 100 and 102, located in such a way that they separately produce the usual light-extinction (LE) signal and one or more light-scattering (LS) signals (from detection over one or more ranges of solid angle) whenever a particle 12 passes through the active illuminated view volume. Detector 100 ($D_{LE}$) in FIG. 4 is used to produce the light-extinction response signal, as described above. For purposes of simplicity, most of the description and discussion which follow assume that only a single detector 102 ($D_{LS}$) is utilized to produce a light scattering (LS) response. However, generalization of this case to include more than one LS response signal may be desirable. The single detector 102 ($D_{LS}$) which is used to produce the LS response, utilizing a particular selected range of scattering solid angles, is shown in FIG. 4.

Specifically, the present invention explicitly includes an electronic means for "conditioning" the LS signal before it is combined with the LE signal, in order to produce a final signal which can be optimally analyzed in order to obtain most reliably the size of each detected particle. The conditioning of the LS signal in general may be required in order to accommodate particles of widely differing composition, for which the magnitude of the light scattering signal (unlike that of light extinction) can be expected to vary significantly with particle composition, for a given size, as discussed above.

The present invention simultaneously combines, by electronic means, the LS signal, with the option of preconditioning it, with the LE signal, thereby forming a new, single signal. The latter is expected to be substantially similar to the LE signal alone in the case of particles which fall into the normal size range of an LE sensor (i.e. diameters≧2 um), where the magnitude of the LE signal substantially exceeds that of the LS signal. However, this new composite signal has properties which are substantially similar to the LS signal alone in the case of particles which normally require the use of an LS sensor (i.e. diameters smaller than one micron, down to the limit of sensitivity of an LS sensor—typically 0.2–0.5 um, depending on the design).

Figure 5:
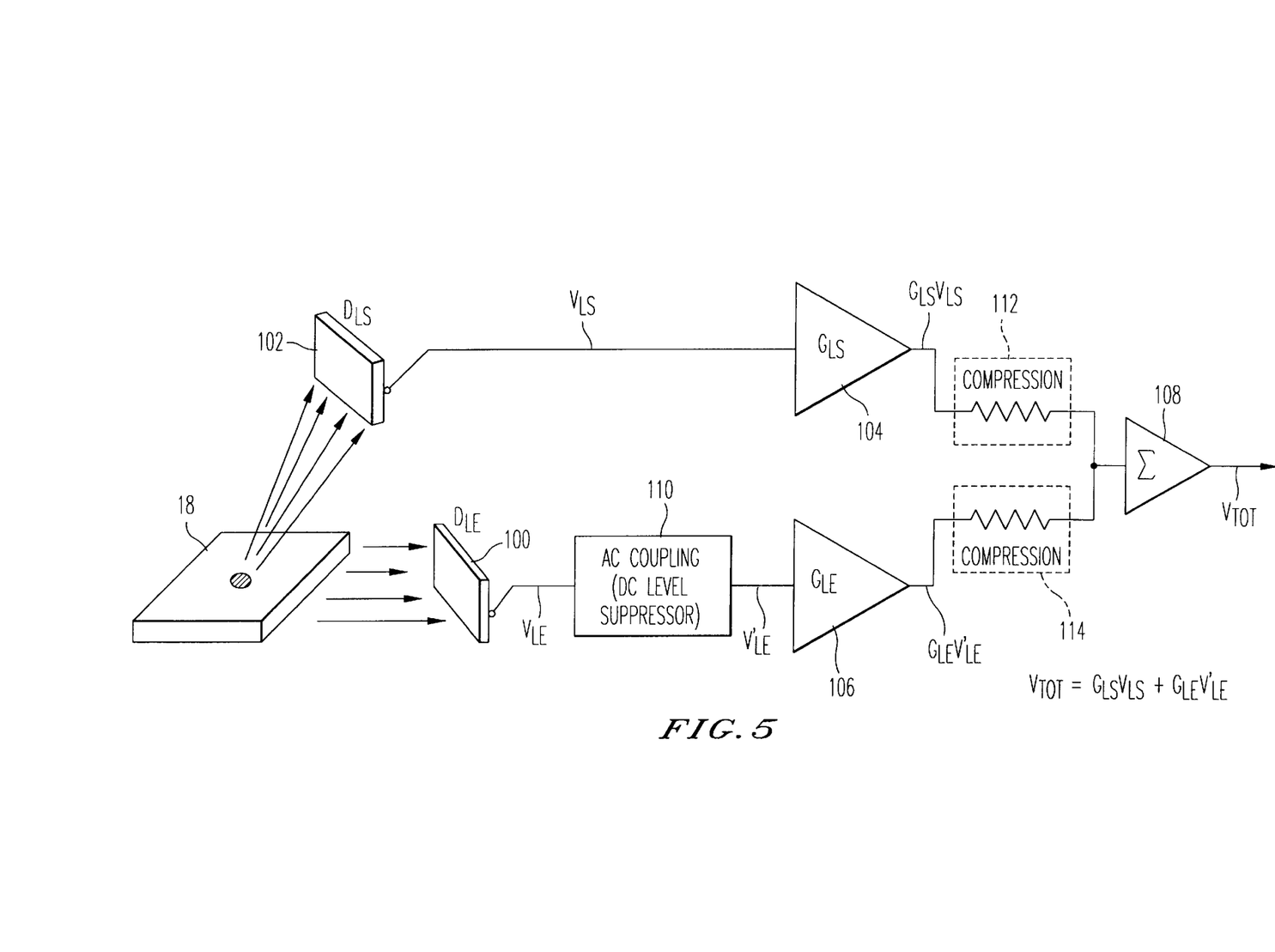
FIG. 5. shows a block diagram of the signal processing system of the present invention.
Figure 6A:
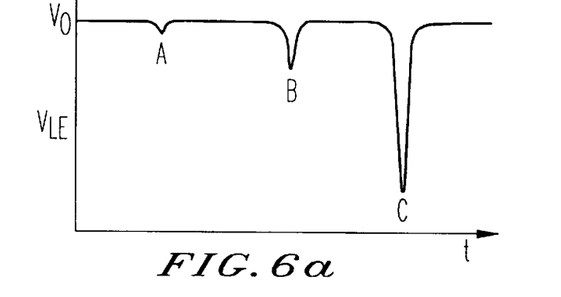
FIGS. 6a, 6b, 6c and 6d illustrate signal pulses produced by the system of the present invention for particles of increasing size.
Figure 6B:
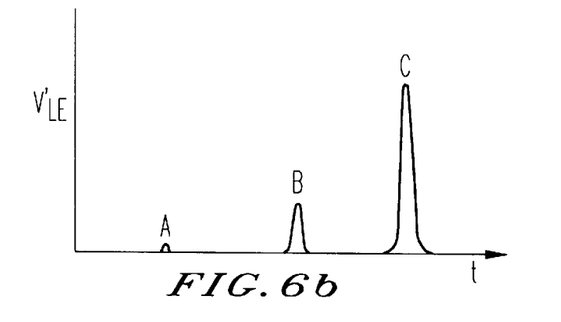
Figure 6C:
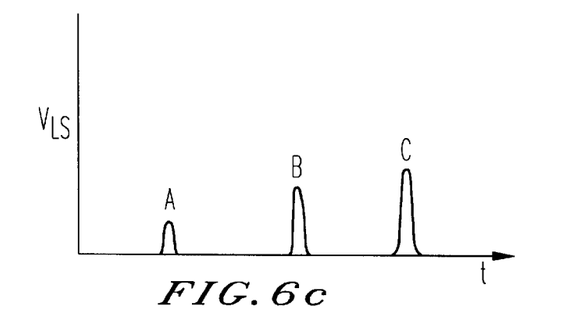
Figure 6D:
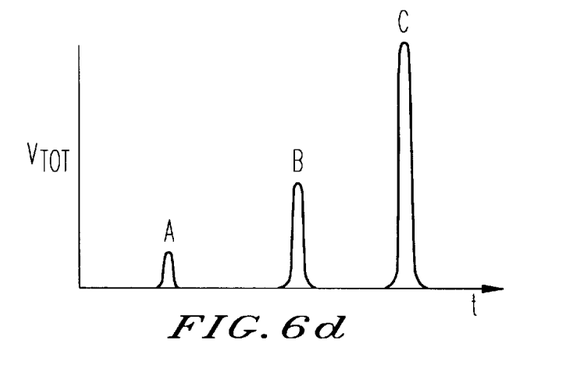

FIG. 5 shows a simplified block diagram of the signal processing scheme which is used in this new sensor design. Here we explicitly allow for the possibility that both the LS signal, $V_{LS}$, and the LE signal, $V_{LE}$, originating from detectors 100 and 102 ($D_{LS}$ and $D_{LE}$, respectively) can be individually conditioned by the use of separate amplifiers 104 and 106, having gains $G_{LS}$ and $G_{LE}$, respectively, before the resulting signals are added together by a summing amplifier 108. In addition, compression circuits 112 and 114 may be used before summing if desired. In the simplest embodiment, discussed below, both gains $G_{LS}$ and $G_{LE}$ would be chosen to be unity (1). FIGS. 6a–d show, in simplified, idealized form signals $V_{LE}$, $V_{LE'}$, $V_{LS}$, and $V_{TOT}$, as defined in FIG. 5.

Three signal pulses are shown in FIGS. 6a–d, corresponding to the response produced by three individual particles of monotonically increasing size—A, B and C. The first particle (A) which passes through the active view volume of the sensor is assumed to be so small that it produces almost no measurable signal response $V_{LE}$ from the LE detector 100, or the AC-coupled, inverted equivalent (block 110), $V_{LE'}$. However, this small particle yields a significant response $V_{LS}$ from the LS-type detector 102. The third, and largest, particle (C) which passes through the sensor produces a very large response $V_{LE}$ from the LE detector 100. However, the response $V_{LS}$ of scattering-type sensor 102, is assumed to reach "saturation" with respect to larger particles. Therefore, the relative contribution of $V_{LS}$ to the total response of the LS+LE sensor is seen to be smaller for this largest particle (C) than for the smallest one (A), or the intermediate-sized particle (B).

Using this novel, direct combination approach to obtain a new SPOS sensor design, which has not heretofore been described or proposed, one obtains the "best of both worlds" for wide dynamic range particle size analysis. For the smallest particle diameters, it functions substantially like an ordinary LS sensor, because in that part of the size range the signal produced by the LE sensor is negligible. On the other hand, at significantly larger diameters the new system functions substantially like an ordinary LE sensor, because at these larger sizes the signal produced by the LE sensor is much larger than that produced by the LS sensor (which has effectively reached saturation). In the range of particle diameters lying between these two clear-cut extremes, there is a smooth transition in the response of the sensor, from mostly "LS-type" to mostly "LE-type" response. This characteristic is clearly different from the situation which obtains using the VonBargen approach.

An important advantage of this new hybrid sensor design, which we refer to symbolically as "LS+LE", is that it avoids the significant disadvantage of having to process and manipulate two or more individual signal responses depending upon the size of each particle which passes through the active view volume, as described by VonBargen. The resulting electronic system is significantly simpler in design, requiring substantially fewer components and offering potentially better reliability.

Another advantage of our new "LS+LE" hybrid sensor design is that one can now use a relatively low power light source 20 in order to achieve a lower limit in particle diameter, by virtue of the contribution of the LS signal to the combined LS+LE signal. The higher the power of the light source (typically a laser diode), the lower the particle size limit of the sensor. All of the extension to smaller diameters comes from the LS portion of the combined LS+LE signal.

A key feature of this new sensor design involves the inherent flexibility of the way in which the LS and LE signals are combined electronically. In the simplest embodiment, the two individual "starting" signals are simply added together with equal "weighting", or gain, using a summing analog amplifier 108. For this first embodiment of the invention there is no additional "conditioning" required for the LS signal before it is added to the LE signal.

In this way, the composite signal, LS+LE, consists mostly of the LS signal for particle diameters below approx. one micron, where the LE signal is negligible. Conversely, at relatively large diameters—i.e. 10 um, or larger—the composite signal is substantially the same as the LE signal alone, because the LS signal for such larger particles is much smaller than the LE signal, due to the specific electronic compression design which is applied to the scatter signal. (See discussion above regarding the use of compression circuitry for LS sensors.) A specific example of the LS+LE response, compared to the LE response alone, will be illustrated below. In between these two limiting cases, the LS signal falls smoothly as a proportion of the total, combined signal, with increasing particle diameter.

This method of combining the LS and LE signals, which uses simple addition and requires no "conditioning" of the former, is appropriate for sizing particles which have similar scattering properties as those of the "standard" particles which have been used to calibrate the sensor (typically polystyrene latex). That is, this simplest method of combining the two available signals is appropriate when the particles to be measured have a similar index of refraction and absorption at the exciting wavelength as those used to calibrate the system.

Figure 7:
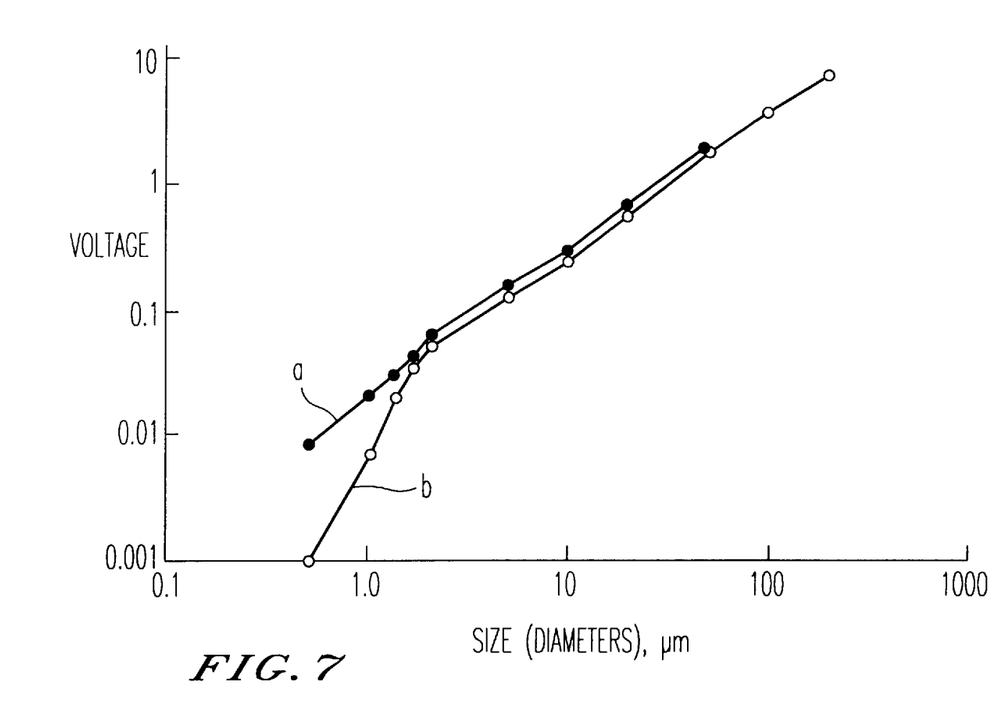
FIGS. 7(a) and 7(b) show typical calibration response curves for a sum-type combination sensor and a light extinction (LE) sensor of the present invention.

FIG. 7 shows typical calibration response curves, log dV vs log d, for a sum-type (LE+LS) combination sensor and a normal light-extinction (LE) sensor. Curve (a) (FIG. 7) refers to the composite response curve of the LS+LE sensor, while curve (b) shows the response based on the LE signal alone. The sensor which produced responses (a) and (b) in to FIG. 7 utilizes a 50-mW laser diode as a source of illumination, and the resulting size range for this LS+LE sensor is approximately 0.5 to 400 um, as shown by sensor response (a) in FIG. 7. Use of the LE signal alone yields a practical lower size limit of approximately 1.5 um. Hence, addition of the LS signal extends the effective lower size limit of this LS+LE sensor to approximately 0.5 um. While this extension in sizing capability might appear to be relatively small, in fact it can be very significant for a number of important particle sizing applications. As can be seen clearly in FIG. 7, the addition of the LS signal to the LE signal ceases to be important for particles larger than about 10 to 20 um. It should be noted that a significant amount of compression was applied to the LS signal before it was added to the LE signal, as shown by curve (a) in FIG. 7.

A similar LE+LS, sum-type response (calibration) curve is obtained using a lower power laser diode light source—5 mW, instead of 50 mW. This produces a proportionately smaller LS signal for a given particle size, which raises the minimum detectable particle diameter. Indeed, the practical lower size limit of this sensor is now only about 1.0 um, while the upper size limit, determined by the LE signal, remains the same (nom. 400 microns).

However, the smallest measurable particle size which is thereby achieved using our new LS+LE invention, using a standard, low-power laser diode light source, is still smaller than the limiting value which is normally achievable in a "conventional" sensor, using only the LE signal, with the same laser diode source. Conversely, if one is prepared to use a light source of even higher power (i.e. >50 mW), then the lowest measurable particle diameter can be reduced below 0.5 um, given the greater magnitude of the LS signal response which can thereby be obtained.

For efficient size analysis of particles which differ substantially in optical properties from those used to calibrate the system, conditioning of the LS signal before combination with the LE signal is highly recommended. This results in a second embodiment of this invention. Two examples are useful to illustrate this point.

In the first example, we assume that the particles of interest have an index of refraction significantly higher than that of the "standard" particles used to calibrate the system, but that they do not absorb incident light significantly more than the standard particles. In this case the LS signal can be expected to be stronger than that produced by the standard particles of the same size, assuming that the index of refraction of the dispersing fluid (liquid or gas) is lower than that of the standard particles. Hence, it is desirable to reduce the size of the LS signal before it is added to the LE signal by the summing amplifier.

The reduction factor in general can be approximated to first order by a simple function of the ratio of refractive indices (i.e. the real, dispersive values) of the particles and dispersing fluid, using the Mie theory of light scattering. The reduction factor will, in general, also depend somewhat on the size of the particles in question and the range of solid angles over which the scattered light is collected. In principle, the approximate factor by which the LS signal should be reduced before being added to the LE signal can be precalculated, stored in the system computer of the instrument and supplied to the electronic signal conditioning system as a variable attenuation (i.e. gain <1) of the LS signal. This process of "conditioning" the LS signal response before adding it to the LE response can be performed by analog circuitry or, better yet, using digital techniques, for example involving the use of one or more digital signal processors (DSPs), thereby providing more flexibility.

In the second example, we assume that the particles of interest are "dark" compared to the standard particles which have been used to calibrate the system—i.e. that they strongly absorb light of the incident wavelength. One example, drawn from the field of contamination analysis, involves carbonaceous "dirt" particles, produced by combustion and found in lubricating or hydraulic oils. Another example would be colored pigment particles, used in paint formulations. A third example might be ceramic or refractory particles.

For these absorbing particles the LS signal component, which is required for measurement of the smallest (submicron) particles in the distribution, is expected to be significantly smaller than the signal which would be obtained from "normal" particles of the same size, which are not strongly absorbing. If those "normal" particles have a real index of refraction similar to that of the standard calibration particles, then the resulting LS signal for the absorbing particles will be smaller than that produced by the standard particles, and a correction factor greater than unity (i.e. gain >1) should be applied to the LS signal before it is added to the LE signal.

In principle, one can use a simple theory of light absorption to calculate a numerical estimate of the effect of absorbance in attenuating the light scattering response, dV, which would normally be expected for particles of each size over the effective size range. As described above for the case of strongly scattering particles, these factors could be pre-stored in the computer of the analyzer and used to condition the resulting LS signal before it is added to the LE response, using either adjustable-gain analog amplifiers and other elements or digital components and circuits, perhaps using one or more DSPs.

On the other hand, if the "normal" particles have a real index of refraction which is significantly different from that of the standard calibration particles, then the resulting LS signal for the absorbing particles may be either smaller or larger than that produced by the standard particles. The outcome will depend on the relative sizes of the effects of the absorbance phenomenon, which always decreases the LS signal, and the real index of refraction, where a higher ratio of particle-to-fluid index increases the LS signal and a lower ratio decreases it. Again, in principle one can precalculate and store several sets of numerical factors (as a function of particle diameter), each of which applies to a different kind of sample material. The relevant set of adjustment factors can later be automatically retrieved and utilized by the computer system, in order to adjust the size of the LS signal before it is added to the LE signal, using simple, well-known mathematical interpolation techniques.

The reason for the decrease in the LS signal with increasing particle absorbance should be evident. The net scattering intensity which is produced by a particle is the result of the superposition (i.e. coherent addition) of all of the individual scattered wavelets which are produced by each of the polarizable electrons located throughout the particle. The absorption of light by the particle occurs in two stages. First, the incident light which reaches any point inside the particle is partially attenuated by passage through a portion of the particle, resulting in a lower level of scattering intensity originating from that point. Second, given the scattering which originates from a given point within the particle, the intensity is reduced as the scattering wavelet passes through the particle to reach the detector outside.

In conclusion, for optimal use of the SPOS method for particle size analysis over the widest variety of applications, it is necessary to achieve the widest possible size range using a sensor of simplest possible design. In particular, one seeks a technological design which provides the highest possible sensitivity—i.e. lowest practical minimum detectable particle diameter—together with the largest possible dynamic range—i.e. highest maximum diameter. It is toward this goal of expanded range of particle size analysis through the use of a straightforward SPOS design that this invention is directed. The automatic, electronic combination of LS and LE sensor signals into a single, composite signal response represents a new and novel way in which the above goals can be reached through an inexpensive, easily implemented design.

Although the invention has been described with reference to a particular embodiment, it is to be appreciated that various adaptations and modifications may be made and the invention is only to be limited by the appended claims.

The invention claimed is:

1. Apparatus for counting and sizing particles, including,
    first means for providing a light extinction (LE) signal representative of the particles, said first means including a light extinction sensor,
    second means for providing a light scattering (LS) signal representative of the particles, said second means including a light scattering sensor, and
    means for combining a light scattering signal and the light extinction signal to form a single composite signal, wherein the single composite signal for particle sizes in an upper range of particle sizes, as typically measured by the light extinction sensor, consists primarily of said light extinction (LE) signal, said light scattering (LS) signal being much smaller than said light extinction (LE) signals for said particle sizes in said upper range, wherein the single composite signal for particle sizes in a lower range of particle sizes, as typically measured by the light scattering sensor, consists primarily of said light scattering (LS) signal, said light extinction signal (LE) being negligible for said particle sizes in said lower range, and wherein the single composite signal has an output representing the combined light extinction (LE) signal and light scattering (LS) signal for particle sizes in a middle range of particle sizes.

2. The apparatus of claim 1, wherein the means for combining consists of an analog summing amplifier.

3. The apparatus of claim 1, wherein said first means comprises electronic means for adjusting the magnitude of said light scattering (LS) signal.

4. The apparatus of claim 3, wherein said electronic means for adjusting the magnitude of the light scattering signal provides for substantially unity gain.

5. The apparatus of claim 3, wherein said electronic means for adjusting the magnitude of the light scattering signal provides a gain of either less than unity, when the particles to be analyzed scatter light better than those particles used to calibrate the means for providing the light scattering (LS) signal, or a gain larger than unity, when the particles scatter light more poorly than those particles used to calibrate the means for providing the light scattering (LS) signal.

6. The apparatus of claim 1, wherein said first and second means comprise electronic compression circuit means.

7. The apparatus of claim 6, wherein the electronic compression circuit means provides a linear single composite signal.

8. The apparatus of claim 6, wherein the electronic compression circuit means provides a non-linear single composite signal.

9. Apparatus for counting and sizing particles, including the following steps:
    providing a light extinction (LE) signal representative of the particles, including using a light extinction sensor,
    providing a light scattering (LS) signal representative of the particles, including using a light scattering sensor, and
    combining a light scattering signal and the light extinction signal to form a single composite signal, and wherein the single composite signal for particle sizes in an upper range of particle sizes typically measured by the light extinction sensor consists primarily of said light extinction (LE) signal, said light scattering (LS) signal being much smaller than said light extinction (LE) signals for said particle sizes in said upper range, and wherein the single composite signal for particle sizes in a lower range of particle sizes as typically measured by the light scattering sensor consists primarily of said light scattering (LS) signal, said light extinction signal (LE) being negligible for said particle sizes in said lower range, and wherein the single composite signal has an output representing the combined light extinction (LE) signal and light scattering (LS) signal for particle sizes in a middle range of particle sizes.

10. The method of claim 9, wherein the step of combining includes the use of an analog summing amplifier.

11. The method of claim 9, wherein said step of providing the light scattering (LS) signal comprises the step of adjusting the magnitude of said light scattering signal.

12. The method of claim 11, wherein the step of adjusting the magnitude of the light scattering signal provides for substantially unity gain.

13. The method of claim 11, wherein the step of adjusting the magnitude of the light scattering signal provides a gain of either less than unity when the particles to be analyzed scatter light better than those particles used to calibrate the light scattering sensor or a gain larger than unity, when the particles scatter light more poorly than those particles used to calibrate the light scattering sensor.

14. The method of claim 9, wherein said steps of providing a light extinction signal and of providing a light scattering signal include a step of compression by an electronic compression circuit.

15. The method of claim 14, wherein the step of compression provides a linear single net signal.

16. The method of claim 14, wherein the step of compression provides a non-linear single net signal.

* * * * *

UNITED STATES PATENT AND TRADEMARK OFFICE
CERTIFICATE OF CORRECTION

PATENT NO.   : 5,835,211
DATED        : November 10, 1998
INVENTOR(S)  : David Wells and David F. Nicoli Page 1 of 1

It is certified that error appears in the above-identified patent and that said Letters Patent is hereby corrected as shown below:

Column 3,
Line 4, "This" should read -- That --.

Column 4,
Line 1, "samples" should read -- sample --.

Column 7,
Line 6, "16," second occurrence, should read -- 10 --.

Claim 1,
Line 8, "a" should be changed to -- the --.
Line 15, "signals" should be changed to -- signal --.

Claim 3,
Line 1, "first" should be changed to --second --.

Claim 9,
Line 15, "signals" should be changed to -- signal --.

Signed and Sealed this

Thirty-first Day of July, 2001

Attest:

*Attesting Officer*

NICHOLAS P. GODICI
*Acting Director of the United States Patent and Trademark Office*